United States Patent [19]
Feild et al.

[11] Patent Number: 5,948,669
[45] Date of Patent: *Sep. 7, 1999

[54] RAT CATHEPSIN K POLYNUCLEOTIDE AND POLYPEPTIDE SEQUENCE

[75] Inventors: John A. Feild, Delran, N.J.; Kimberly Brun, Philadelphia, Pa.

[73] Assignee: SmithKline Beecham Corporation, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/806,959

[22] Filed: Feb. 26, 1997

[51] Int. Cl.⁶ .............................. C12N 5/10; C12N 9/64; C12N 15/57; C12N 15/63
[52] U.S. Cl. .............. 435/226; 435/320.1; 435/325; 536/23.2; 536/24.31
[58] Field of Search .......................... 536/23.2, 24.31; 435/320.1, 325, 226

[56] References Cited

U.S. PATENT DOCUMENTS 5,501,969  3/1996  Hastings et al. ........................ 435/325

FOREIGN PATENT DOCUMENTS

WO 9524182  9/1995  WIPO .
WO 9613523  5/1996  WIPO .
WO 9716177  5/1997  WIPO .

OTHER PUBLICATIONS

Shi et al., "Molecular cloning of human cathepsin O, a novel endoproteinase and homologue of rabbit OC2", *FEBS Letters*, 357, pp. 129–134 (1995).
Accession No. AF010306, Payne et al., "*Rattus norvegicus* cathepsin K mRNA" (1997).
Rantakokko et al., FEBS Letters 393:307–313, 1996.
Tezuka et al., J. Biol. Chem. 269:1106–1109, 1994.
Hadman et al., Oncogene 12:135–142, 1996.
Hill et al., J. Cell. Biochem. 56:118–130, 1994.
Gelb et al., Science 273:1236–1238, 1996.
Drake, et al., "Identification of a Novel Osteoclast–Selective Human Cystein Proteinase", *J. Bone Miner. Res.,* 9:S177, 1994.

*Primary Examiner*—Karen Cochrane Carlson
*Attorney, Agent, or Firm*—William T. Han; William T. King; Charles M. Kinzig

[57] ABSTRACT

Rat cathepsin k polypeptides and polynucleotides and methods for producing such polypeptides by recombinant techniques are disclosed. Also disclosed are methods for utilizing rat cathepsin k polypeptides and polynucleotides in the design of protocols for the treatment of osteoporosis, periodonatal disease, arthritis, cancer, tumor metastasis, and Paget's disease, among others, and diagnostic assays for such conditions.

21 Claims, 1 Drawing Sheet

Nucleotide and Amino Acid sequence from a rat cathepsin k
(SEQ ID NOS: 1 and 2, respectively.)

```
  1 ATGTGGGGGCTCAAGGTTCTGCTGCTACCCGTGGTGAGCTTTGCTCTATCCCCGGAGGAA  60
    M   W   G   L   K   V   L   L   L   P   V   V   S   F   A   L   S   P   E   E

61 ACGCTGGACACGCAGTGGGAGCTGTGGAAGAAGACCCACGGGAAGCAGTACAACAGCAAG 120
    T   L   D   T   Q   W   E   L   W   K   K   T   H   G   K   Q   Y   N   S   K

121 GTGGATGAAATCTCTCGGCGTTTAATTTGGGAAAAAAACCTGAAGAAAATTTCTGTCCAT 180
    V   D   E   I   S   R   R   L   I   W   E   K   N   L   K   K   I   S   V   H

181 AATCTTGAGGCCTCTCTTGGTGCCCATACGTATGAGCTGGCCATGAATCACCTGGGAGAC 240
    N   L   E   A   S   L   G   A   H   T   Y   E   L   A   M   N   H   L   G   D

241 ATGACCAGCGAAGAAGTGGTTCAGAAGATGACTGGACTCAGAGTGCCACCTTCGCGTTCC 300
    M   T   S   E   E   V   V   Q   K   M   T   G   L   R   V   P   P   S   R   S

301 TTCAGTAATGACACTCTCTATACCCCAGAGTGGGAAGGCAGAGTCCCAGACTCCATCGAC 360
    F   S   N   D   T   L   Y   T   P   E   W   E   G   R   V   P   D   S   I   D

361 TATCGAAAGAAAGGCTATGTTACTCCAGTCAAAAACCAGGGCCAGTGTGGTTCCTGTTGG 420
    Y   R   K   K   G   Y   V   T   P   V   K   N   Q   G   Q   C   G   S   C   W

421 GCTTTCAGCTCTGCGGGTGCCCTGGAGGGCCAACTCAAGAAGAAAACTGGCAAACTCTTA 480
    A   F   S   S   A   G   A   L   E   G   Q   L   K   K   K   T   G   K   L   L

481 GCTCTGAGTCCCCAGAATCTTGTGGACTGTGTGTCTGAGAACTATGGCTGTGGAGGCGGC 540
    A   L   S   P   Q   N   L   V   D   C   V   S   E   N   Y   G   C   G   G

541 TATATGACCACTGCCTTCCAATATGTGCAGCAGAATGGAGGCATTGACTCTGAAGACGCT 600
    Y   M   T   T   A   F   Q   Y   V   Q   Q   N   G   G   I   D   S   E   D   A

601 TACCCGTATGTGGGGCAGGATGAAAGTTGTATGTATAACGCCCACGGCAAAGGCAGCTAAG 660
    Y   P   Y   V   G   Q   D   E   S   C   M   Y   N   A   T   A   K   A   A   K

661 TGCAGAGGGTACAGAGAGATCCCTGTGGGAACGAGAAAGCCCTGAAGAGAGCAGTGGCT 720
    C   R   G   Y   R   E   I   P   V   G   N   E   K   A   L   K   R   A   V   A

721 CGGGTAGGACCCGTCTCTGTGTCCATCGATGCAAGCTTGACATCTTTCCAATTTTACAGC 780
    R   V   G   P   V   S   V   S   I   D   A   S   L   T   S   F   Q   F   Y   S

781 AGAGGTGTGTACTATGACGAAAACTGCGACCGTGATAATGTGAACCATGCCGTGTTGGTG 840
    R   G   V   Y   Y   D   E   N   C   D   R   D   N   V   N   H   A   V   L   V

841 GTGGGCTATGGCACCCAGAAGGGAAATAAGTACTGGATAATTAAAAACAGCTGGGGAGAA 900
    V   G   Y   G   T   Q   K   G   N   K   Y   W   I   I   K   N   S   W   G   E

901 AGCTGGGGAAACAAAGGCTATGTTCTCTTGGCTCGGAATAAGAACAATGCCTGTGGCATT 960
    S   W   G   N   K   G   Y   V   L   L   A   R   N   K   N   N   A   C   G   I

961 ACCAACCTGGCCAGCTTCCCCAAGATGTGA 990
    T   N   L   A   S   F   P   K   M   *
```

Nucleotide and Amino Acid sequence from a rat cathepsin k
(SEQ ID NOS: 1 and 2, respectively.)

```
  1 ATGTGGGGGCTCAAGGTTCTGCTGCTACCCGTGGTGAGCTTTGCTCTATCCCCGGAGGAA  60
    M  W  G  L  K  V  L  L  L  P  V  V  S  F  A  L  S  P  E  E

61 ACGCTGGACACGCAGTGGGAGCTGTGGAAGAAGACCCACGGGAAGCAGTACAACAGCAAG 120
    T  L  D  T  Q  W  E  L  W  K  K  T  H  G  K  Q  Y  N  S  K

121 GTGGATGAAATCTCTCGGCGTTTAATTTGGGAAAAAAACCTGAAGAAAATTTCTGTCCAT 180
    V  D  E  I  S  R  R  L  I  W  E  K  N  L  K  K  I  S  V  H

181 AATCTTGAGGCCTCTCTTGGTGCCCATACGTATGAGCTGGCCATGAATCACCTGGGAGAC 240
    N  L  E  A  S  L  G  A  H  T  Y  E  L  A  M  N  H  L  G  D

241 ATGACCAGCGAAGAAGTGGTTCAGAAGATGACTGGACTCAGAGTGCCACCTTCGCGTTCC 300
    M  T  S  E  E  V  V  Q  K  M  T  G  L  R  V  P  P  S  R  S

301 TTCAGTAATGACACTCTCTATACCCCAGAGTGGGAAGGCAGAGTCCCAGACTCCATCGAC 360
    F  S  N  D  T  L  Y  T  P  E  W  E  G  R  V  P  D  S  I  D

361 TATCGAAAGAAAGGCTATGTTACTCCAGTCAAAAACCAGGGCCAGTGTGGTTCCTGTTGG 420
    Y  R  K  K  G  Y  V  T  P  V  K  N  Q  G  Q  C  G  S  C  W

421 GCTTTCAGCTCTGCGGGTGCCCTGGAGGGCCAACTCAAGAAGAAAACTGGCAAACTCTTA 480
    A  F  S  S  A  G  A  L  E  G  Q  L  K  K  K  T  G  K  L  L

481 GCTCTGAGTCCCCAGAATCTTGTGGACTGTGTGTCTGAGAACTATGGCTGTGGAGGCGGC 540
    A  L  S  P  Q  N  L  V  D  C  V  S  E  N  Y  G  C  G  G  G

541 TATATGACCACTGCCTTCCAATATGTGCAGCAGAATGGAGGCATTGACTCTGAAGACGCT 600
    Y  M  T  T  A  F  Q  Y  V  Q  Q  N  G  G  I  D  S  E  D  A

601 TACCCGTATGTGGGGCAGGATGAAAGTTGTATGTATAACGCCACGGCAAAGGCAGCTAAG 660
    Y  P  Y  V  G  Q  D  E  S  C  M  Y  N  A  T  A  K  A  A  K

661 TGCAGAGGGTACAGAGAGATCCCTGTGGGGAACGAGAAAGCCCTGAAGAGAGCAGTGGCT 720
    C  R  G  Y  R  E  I  P  V  G  N  E  K  A  L  K  R  A  V  A

721 CGGGTAGGACCCGTCTCTGTGTCCATCGATGCAAGCTTGACATCTTTCCAATTTTACAGC 780
    R  V  G  P  V  S  V  S  I  D  A  S  L  T  S  F  Q  F  Y  S

781 AGAGGTGTGTACTATGACGAAAACTGCGACCGTGATAATGTGAACCATGCCGTGTTGGTG 840
    R  G  V  Y  Y  D  E  N  C  D  R  D  N  V  N  H  A  V  L  V

841 GTGGGCTATGGCACCCAGAAGGGAAATAAGTACTGGATAATTAAAAACAGCTGGGGAGAA 900
    V  G  Y  G  T  Q  K  G  N  K  Y  W  I  I  K  N  S  W  G  E

901 AGCTGGGGAAACAAAGGCTATGTTCTCTTGGCTCGGAATAAGAACAATGCCTGTGGCATT 960
    S  W  G  N  K  G  Y  V  L  L  A  R  N  K  N  N  A  C  G  I

961 ACCAACCTGGCCAGCTTCCCCAAGATGTGA 990
    T  N  L  A  S  F  P  K  M  *
```

FIG. 1

RAT CATHEPSIN K POLYNUCLEOTIDE AND POLYPEPTIDE SEQUENCE

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to cysteine proteases family, hereinafter referred to as rat cathepsin k. The invention also relates to inhibiting or activating the action of such polynucleotides and polypeptides.

BACKGROUND OF THE INVENTION

Bone is composed of a protein matrix into which an inorganic mineral component is incorporated. Bone resorption requires both the dissolution of the inorganic mineral component as well as proteolytic degradation of the protein matrix. Cysteine proteases are thought to be involved in bone resorption since prototypic inhibitors of cysteine proteases can prevent osteoclast mediated bone resorbtion using in vitro and in vivo models. A novel cysteine protease, termed cathepsin K, has been identified from rabbit (Tezuka, K-i., Tezuka, Y., Maejima, A., Sato, T., Nemoto, K., Kamioka, H., Hakeda, Y., and Kumegawa, M. (1994) *J. Biol. Chem.* 269, 1106–1109), human (Shi, G-P., Chapman, H. A., Bhairi, S. M., DeLeeuw, C., Reddy, V. Y., and Weiss, S. J. (1995) *FEBS Lett.* 357, 129–134; Bromme, D. and Okamoto, K. (1995) *Biol. Chem.* Hoppe-Seyler 376, 379–384; Li, Y. P., Alexander, M. B., Wucherpfennis, A. L., Chen, W., Yelick, P., and Stashenko, P. (1994) *Mol. Biol. Cell*5, 335a; Inaoka, T., Bilbe, G., Ishibashi, O., Tezuka, K-i., Kamegawa, M., and Kokubo, T. (1995) *Biochem. Biophys. Res. Commun.* 206, 89–96), and murine tissues (Rantakokko, J., Aro, H. T., Savontaus, M., and Vuorio, E. (1996) *FEBS Letters*393, 307–313). Cathepsin K was found to be abundantly and selectively expressed in osteoclasts (Drake, F., et al, *J. Biol. Chem.* 271:12511–12516, 1996). Other closely related members of the cysteine protease family (cathepsins S, L, B) are either very low or absent in osteoclasts. The high level, localized expression of cathepsin K in osteoclasts strongly suggests a role in bone resorption. Selective inhibitors of human cathepsin K could be useful in the treatment of a number of diseases involving bone loss, such as osteoporosis, periodontal disease, arthritis, and Paget's disease. Assays to evaluate potential cathepsin K inhibitors requires large amounts of purified enzyme which can be achieved through the cloning, expression and purification of recombinant molecules. Characterization and development of inhibitors of human cathepsin K for prevention of bone resorption utilizes both in vitro and in vivo animal model systems, particularly from rat. The cloning and expression of the rat cathepsin K ortholog is of significant value in assessing species differences in pharmacological activity of inhibitors between rat and human cathepsin K, and for identifying those compounds that possess inhibitory activity against either rat cathepsin K, human cathepsin K, or both.

This indicates that these cysteine proteases have an established, proven history as therapeutic targets. Clearly there is a need for identification and characterization of further members of cysteine proteases family which can play a role in preventing, ameliorating or correcting dysfunctions or diseases, including, but not limited to, osteoporosis, periodonatal disease, arthritis, cancer, tumor metastasis, and Paget's disease.

SUMMARY OF THE INVENTION

In one aspect, the invention relates to rat cathepsin k polypeptides and recombinant materials and methods for their production. Another aspect of the invention relates to methods for using such rat cathepsin k polypeptides and polynucleotides. Such uses include the treatment of osteoporosis, periodonatal disease, arthritis, cancer, tumor metastasis, and Paget's disease, among others. In still another aspect, the invention relates to methods to identify agonists and antagonists using the materials provided by the invention, and treating conditions associated with rat cathepsin k imbalance with the identified compounds. Yet another aspect of the invention relates to diagnostic assays for detecting diseases associated with inappropriate rat cathepsin k activity or levels.

BRIEF DESCRIPTION OF THE DRAWINGS

FIG. 1 shows the nucleotide and deduced amino acid sequence from a rat cathepsin k. SEQ ID NOS: 1 and 2.

DESCRIPTION OF THE INVENTION

Definitions

The following definitions are provided to facilitate understanding of certain terms used frequently herein.

"Rat cathepsin k" refers, among others, generally to a polypeptide having the amino acid sequence set forth in SEQ ID NO: 2 or an allelic variant thereof.

"Rat cathepsin k activity or rat cathepsin k polypeptide activity" or "biological activity of the rat cathepsin k or rat cathepsin k polypeptide" refers to the metabolic or physiologic function of said rat cathepsin k including similar activities or improved activities or these activities with decreased undesirable side-effects. Also included are antigenic and immunogenic activities of said rat cathepsin k.

"Rat cathepsin k gene" refers to a polynucleotide having the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRASLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et aL., *Nucleic Acids Research* (1984) 12(1): 387), BLASTP, BLASTN, FASTA (Atschul, S.F. et al., *J Molec Biol* (1990) 215:403).

Polypeptides of the Invention

In one aspect, the present invention relates to rat cathepsin k polypeptides. The rat cathepsin k polypeptides include the polypeptide of SEQ ID NO: 2; as well as polypeptides comprising the amino acid sequence of SEQ ID NO: 2; and polypeptides comprising the amino acid sequence which have at least 80% identity to that of SEQ ID NO: 2 over its entire length, and still more preferably at least 90% identity, and even still more preferably at least 95% identity to SEQ ID NO: 2. Also included within rat cathepsin k polypeptides are polypeptides having the amino acid sequence which have at least 80% identity to the polypeptide having the amino acid sequence of SEQ ID NO: 2 over its entire length, and still more preferably at least 90% identity, and still more preferably at least 95% identity to SEQ ID NO: 2. Preferably rat cathepsin k polypeptide exhibit at least one biological activity of rat cathepsink.

The rat cathepsin k polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the rat cathepsin k polypeptides are also included in the invention. A fragment is a polypeptide having an amino acid sequence that entirely is the same as part, but not all, of the amino acid sequence of the aforerentioned rat cathepsin k polypeptides. As with rat cathepsin k polypeptides, fragments may be "freestanding," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of rat cathepsin k polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of rat cathepsin k polypeptides, except for deletion of a continuous series of residues that includes the amino terminus, or a continuous series of residues that includes the carboxyl termiinus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate rat cathepsin k activity, including those with a similar activity or an improved activity, or with a decreased undesirable activity. Also included are those that are antigenic or immnunogenic in an animal, especially in a human.

Preferably, all of these polypeptide fragments retain the biological activity of the rat cathepsin k, including antigenic activity. Variants of the definedsequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The rat cathepsin k polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to rat cathepsin k polynucleotides. Rat cathepsin k polynucleotides include isolated polynucleotides which encode the rat cathepsin k polypeptides and fragments, and polynucleotides closely related thereto. More specifically, rat cathepsin k polynucleotide of the invention include a polynucleotide comprising the nucleotide sequence set forth in SEQ ID NO: 1 encoding a rat cathepsin k polypeptide of SEQ ID NO: 2, and polynucleotide having the particular sequence of SEQ ID NO: 1. Rat cathepsin k polynucleotides further include a polynucleotide comprising a nucleotide sequence that has at least 80% identity to a nucleotide sequence encoding the rat cathepsin k polypeptide of SEQ ID NO: 2 over its entire length, and a polynucleotide that is at least 80% identical to that having SEQ ID NO: 1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under rat cathepsin k polynucleotides are a nucleotide sequence which has sufficient identity to a nucleotide sequence contained in SEQ ID NO: 1 to hybridize under conditions useable for amplification or for use as a probe or marker. The invention also provides polynucleotides which are complementary to such rat cathepsin k polynucleotides.

Rat cathepsin k of the invention is structurally related to other proteins of the cysteine proteases, as shown by the results of sequencing the cDNA encoding rat cathepsin k. The cDNA sequence contains an open reading frame encoding a polypeptide of 329 amino acids. Amino acid of sequence of FIG. 1 (SEQ ID NO: 2) has about 92.4% identity (using FASTA) in 329 amino acid residues with human cathepsin K (Drake, F. et al., J. Bone Miner. Res. 9:S177, 1994). Furthermore, rat cathepsin K is 93.6% identical to rabbit cathepsin K over 329 amino acids (Tezuka, K. et al., *J. Biol. Chem* 269:1106, 1994) Nucleotide sequence of FIG. 1 (SEQ ID NO: 1) has about 87.9% identity (using FASTA) in 990 nucleotide residues with human cathepsin K (Drake, F., et al. J. Bone Miner. Res. 9:S177, 1994). Furthermore, rat cathepsin K is 88.1% identical to rabbit cathepsin K over 990 nucleotides (Tezuka, K. et al., *J. Biol. Chem.* 269:1106, 1994)

One polynucleotide of the present invention encoding rat cathepsin k may be obtained using standard cloning and screening, from a cDNA library derived from mRNA in cells of rat bone (spine) using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp: 3–174). Polynucleotides of the invention can also be obtained from natural sources such as genomic DNA libraries or can be synthesized using well known and commercially available techniques.

The nucleotide sequence encoding rat cathepsin k polypeptide of SEQ ID NO: 2 may be identical over its entire length to the coding sequence set forth in FIG. 1 (SEQ ID NO: 1), or may be a degenerate form of this nucleotide sequence encoding the polypeptide of SEQ ID NO: 2, or may be highly identical to a nucleotide sequence that encodes the polypeptide of SEQ ID NO: 2. Preferably, the polynucleotides of the invention comprise a nucleotide sequence that is highly identical, at least 80% identical, with a nucleotide sequence encoding a rat cathepsin k polypeptide, or at least 80% identical with the sequence contained in FIG. 1 (SEQ ID NO: 1) encoding rat cathepsin k polypeptide, or at least 80% identical to a nucleotide sequence encoding the polypeptide of SEQ ID NO: 2.

When the polynucleotides of the invention are used for the recombinant production of rat cathepsin k polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions.

For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding rat cathepsin k variants comprise the amino acid sequence rat cathepsin k polypeptide of FIG. 1 (SEQ ID NO: 2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO: 1, may be used as hybridization probes for cDNA and genomic DNA, to isolate full-length cDNAs and genomic clones encoding rat cathepsin k polypeptide and to isolate cDNA and genomic clones of other genes that have a high sequence similarity to the rat cathepsin k gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding rat cathepsin k comprises the steps of screening an appropriate library under stingent hybridization conditions with a labeled probe having the SEQ ID NO: 1 or a fragment thereof; and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1× SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et aL, *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C 127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the rat cathepsin k polypeptide is to be expressed for use in screening assays, generally, it is preferred that the polypeptide be produced at the surface of the cell. In this event, the cells may be harvested prior to use in the screening assay. If rat cathepsin k polypeptide is secreted into the medium, the medium can be recovered in order to recover and purify the polypeptide; if produced intracellularly, the cells must first be lysed before the polypeptide is recovered. rat cathepsin k polypeptides can be recovered and purified from recombinant cell cultures by well-known methods including ammonium sulfate or ethanol precipitaction, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of rat cathepsin k polynucleotides for use as diagnostic reagents. Detection of a mutated form of rat cathepsin k gene associated with a dysfunction will provide a diagnostic tool that can add to or define a diagnosis of a disease or susceptibility to a disease which results from under-expression, over-expression or altered expression of rat cathepsin k. Individuals carrying mutations in the rat cathepsin k gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled rat cathepsin k nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985) 230:1242. Sequence changes at specific locations may also be revealed by nuclease protection assays, such as RNase and S1 protection or the chemical cleavage method. See Cotton et al., Proc Natl Acad Sci USA (1985) 85:4397–4401. In another embodiment, an array of oligonucleotides probes comprising rat cathepsin k nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp610–613 (1996)).

The diagnostic assays offer a process for diagnosing or determining a susceptibility to osteoporosis, periodonatal disease, arthritis, cancer, tumor metastasis, and Paget's disease through detection of mutation in the rat cathepsin k gene by the methods described.

In addition, osteoporosis, periodonatal disease, arthritis, cancer, tumor metastasis, and Paget's disease, can be diagnosed by methods comprising determining from a sample derived from a subject an abnormally decreased or increased level of rat cathepsin k polypeptide or rat cathepsin k mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an rat cathepsin k polypeptide, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the rat cathepsin k polypeptides. The term "immunosnospecific" means that the antibodies have substantial greater affinity for the polypeptides of the invention than their affinity for other related polypeptides in the prior art.

Antibodies generated against the rat cathepsin k polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybriodoma technique (Kozbor et al., Immunology Today (1983) 4:72) and the EBV-hybridoma technique (Cole et al, MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against rat cathepsin k polypeptides may also be employed to treat osteoporosis, periodonatal disease, arthritis, cancer, tumor metastasis, and Paget's disease, among others.

Vaccines

Another aspect of the invention relates to a method for inducing an immunological response in a mammal which comprises inoculating the mammal with rat cathepsin k polypeptide, or a fragment thereof, adequate to produce antibody and/or T cell immune response to protect said animal from osteoporosis, periodonatal disease, arthritis, cancer, tumor metastasis, and Paget's disease, among others. Yet another aspect of the invention relates to a method of inducing immunological response in a mammal which comprises, delivering rat cathepsin k polypeptide via a vector directing expression of rat cathepsin k polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a rat cathepsin k polypeptide wherein the composition comprises a rat cathepsin k polypeptide or rat cathepsin k gene. The vaccine formulation may further comprise a suitable carrier. Since rat cathepsin k polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The rat cathepsin k polypeptide of the present invention may be employed in a screening process for compounds which activate (agonists) or inhibit activation of (antagonists, or otherwise called inhibitors) the rat cathepsin k polypeptide of the present invention. Thus, polypeptides of the invention may also be used to assess identify agonist or antagonists from, for example, cells, cell-free preparations, chemical libraries, and natural product mixtures. These agonists or antagonist may be natural substrates, ligands, receptors, etc., as the case may be, of the polypeptide of the present invention; or may be structural or functional miretics of the polypeptide of the present invention. See Coligan et al., *Current Protocols in Inununology* 1(2): Chapter 5 (1991).

Rat cathepsin k polypeptides are ubiquitous in the mammalian host and are responsible for many biological functions, including many pathologies. Accordingly, it is desirous to find compounds and drugs which stimulate rat cathepsin k polypeptide on the one hand and which can inhibit the function of rat cathepsin k polypeptide on the other hand. In general, agonists are employed for therapeutic and prophylactic purposes for such conditions as osteoporosis, periodonatal disease, arthritis, cancer, tumor metastasis, and Paget's disease. Antagonists may be employed for a variety of therapeutic and prophylactic purposes for such conditions as osteoporosis, periodonatal disease, arthritis, cancer, tumor metastasis, and Paget's disease.

In general, such screening procedures may involve using appropriate cells which express the rat cathepsin k polypeptide or respond to rat cathepsin k polypeptide of the present invention. Such cells include cells from mammals, yeast, Drosophila or *E. coli*. Cells which express the rat cathepsin k polypeptide (or cell membrane containing the expressed polypeptide) or respond to rat cathepsin k polypeptide are then contacted with a test compound to observe binding, or stimulation or inhibition of a functional response. The ability of the cells which were contacted with the candidate compounds is compared with the same cells which were not contacted for rat cathepsin k activity.

The encoded polypeptide and processed forms are suitable for screening assays both to identify rat cathepsin K inhibitors and to assess activity of compounds prior to testing in in vitro functional assays or in vivo testing in the rat. Screening assays may monitor the proteolytic cleavage, or inhibition thereof, of a suitable substrate such as a protein or peptide which may contain a chromogenic or fluorogenic tag. Compounds selected from screening may be tested in in vitro functional assays or in vivo. In vitro assays useful in this regard include bone resorption assays, such as the Fetal Rat Long Bone assay, Fetal Rat Parietal Bone assay, or monitoring the formation of bone resorption lacunae by isolated rat osteoclasts on bone slices ("pit" assay). Examples of in vivo assays include the PTH-treated thyroparathyroidectomized rat and the ovariectomized rat. The encoded polypeptide and processed forms are also useful for structural characterization of the protein and for obtaining antibodies to rat cathepsin K.

The assays may simply test binding of a candidate compound wherein adherence to the cells bearing the rat cathepsin k polypeptide is detected by means of a label directly or indirectly associated with the candidate compound or in an assay involving competition with a labeled competitor. Further, these assays may test whether the candidate compound results in a signal generated by activation of the rat cathepsin k polypeptide, using detection systems appropriate to the cells bearing the rat cathepsin k polypeptide. Inhibitors of activation are generally assayed in the presence of a known agonist and the effect on activation by the agonist by the presence of the candidate compound is observed. Standard methods for conducting such screening assays are well understood in the art.

Examples of potential rat cathepsin k polypeptide antagonists include antibodies or, in some cases, oligonucleotides or proteins which are closely related to the ligands, substrates, receptors, etc., as the case may be, of the rat cathepsin k polypeptide, e.g., a fragment of the ligands, substrates, receptors, or small molecules which bind to the polypetide of the present invention but do not elicit a response, so that the activity of the polypeptide is prevented.

Prophylactic and Therapeutic Methods

This invention provides methods of treating an abnormal conditions related to both an excess of and insufficient amounts of rat cathepsin k polypeptide activity.

If the activity of rat cathepsin k polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the rat cathepsin k polypeptide, or by inhibiting a second signal, and thereby alleviating the abnormal condition.

In another approach, soluble forms of rat cathepsin k polypeptides still capable of binding the ligand in competition with endogenous rat cathepsin k polypeptide may be administered. Typical embodiments of such competitors comprise fragments of the rat cathepsin k polypeptide.

In still another approach, expression of the gene encoding endogenous rat cathepsin k polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of rat cathepsin k and its activity, several approaches are also available. One approach comprises administering to a subject a therapeutically effective amount of a compound which activates rat cathepsin k polypeptide, i.e., an agonist as described above, in combination with a pharmaceutically acceptable carrier, to thereby alleviate the abnormal condition. Alternatively, gene therapy may be employed to effect the endogenous production of rat cathepsin k by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of rat cathepsin k polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

Muscle and surrounding tissue was dissected away from a rat spine. Total RNA was extracted from the bone by homogenization in TriZOL Reagent (GIBCO/BRL, Gaithersburg, Md.) and concentrated by isopropanol precipitation. Poly A+mRNA was prepared by oligo-dT chromatography. Degenerate PCR primers were designed based on conserved region of human, rabbit and mouse cDNA at the extreme 5' and 3' ends of the coding sequence. These primers are complementary to the first 21 bases of the coding region (SB9214) starting with ATG and the last 21 bases ending with the stop codon TGA (SB9216). Using the Life Technologies Stratascript II Pre-amplification System (GIBCO/BRL, Gaithersburg, Md.) and the polymerase chain reaction with the above primers a 990 base pair DNA fragment was amplified and subcloned into the pCR2 vector (Invitrogen, San Diego, Calif.) Sequencing of two independently derived clones of this fragment revealed approximately 88% homology to human cathepsin K and only 70% homology to human cathepsin S. To confirm the sequence a second RT-PCR derived clone was isolated from rat arthritic ankle cDNA. The sequence of this clone matched identically with the original (clone designation RCK2). To confirm the sequence at the 3' end a primer was designed based on a conserved portion of the 3' untranslated region of the human and rabbit cDNA. This primer (SB2268) was used along with a rat gene specific internal primer (SB9737) to amplify by RT-PCR a 360 base pair fragment from rat bone (spine) cDNA. Sequencing of this 3' fragment confirmed that the sequence of the original clone was correct.

This sequence has been expressed in heterologus systems (*E. coli* and baculovirus) to allow high level protein production. Recombinant protein produced in and purified from these systems is useful in screening assays to identify inhibitors of catalytic activity as well as a source of material for structural studies and antibody production.

What is claimed is:

1. An isolated polynucleotide comprising a nucleotide sequence that has at least 90% identity to a nucleotide sequence encoding the polypeptide of SEQ ID NO: 2 over its entire length; wherein the identity is calculated using FASTA, and parameters are set such that sequences are aligned so that the highest order match is obtained.

2. The polynucleotide of claim 1 wherein said nucleotide sequence is at least 90% identical to that contained in SEQ ID NO: 1; wherein the identity is calculated using FASTA, and parameters are set such that sequences are aligned so that the highest order match is obtained.

3. The polynucleotide of claim 2 wherein said nucleotide sequence comprises the sequence which encodes the polypeptide of SEQ ID NO: 2 contained in SEQ ID NO: 1.

4. A polynucleotide probe or primer comprising at least 15 contiguous nucleotides of the polynucleotide of claim 2.

5. A polynucleotide of claim 1 which comprises a nucleotide sequence that has at least 95% identity to a nucleotide sequence encoding the polypeptide of SEQ ID NO: 2 over its entire length; wherein the identity is calculated using FASTA, and parameters are set such that sequences are aligned so that the highest order match is obtained.

6. The polynucleotide of claim 1 wherein said nucleotide sequence is at least 95% identical to that contained in SEQ ID NO: 1; wherein the identity is calculated using FASTA, and parameters are set such that sequences are aligned so that the highest order match is obtained.

7. A polynucleotide any one of claims 1, 2, 3, 4, 5, or 6 which is DNA or RNA.

8. The polynucleotide consisting of the polynucleotide of SEQ ID NO: 1.

9. An isolated DNA or RNA molecule comprising a DNA or RNA sequence encoding a polypeptide comprising an amino acid sequence, which has at least 95% identity with the polypeptide of SEQ ID NO: 2, operably linked to expression control sequences, such that said polypeptide is produced when said isolated DNA or RNA molecule is present in a compatible host cell; and wherein the identity is calculated using FASTA, and parameters are set such that sequences are aligned so that the highest order match is obtained.

10. A polynucleotide which is the complement of the isolated polynucleotide of any one of claims 1, 2, 3, 8, 4, 9, 5, or 6.

11. A process for producing a cell which produces a polypeptide comprising transforming or transfecting a host cell with the DNA or RNA sequence of claim 9 such that the host cell, under appropriate culture conditions, produces said polypeptide.

12. Cells produced by the process of claim 11.

13. An isolated host cell comprising the isolated DNA or RNA molecule of claim 9.

14. A process for producing a polypeptide comprising culturing a host of claim 13 and under conditions sufficient for the production of said polypeptide.

15. The process of claim 14 which further includes recovering the polypeptide from the culture.

16. A polypeptide prepared by the method of claim 15.

17. A polynucleotide comprising a DNA sequence obtainable by screening an appropriate library under stringent hybridization conditions; wherein stringent hybridization conditions are under overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1× SSC at about 65° C.; with a probe having the sequence of SEQ ID NO: 1 or a fragment thereof; and isolating said DNA sequence.

18. An isolated polypeptide comprising an amino acid sequence which is at least 95% identical to the amino acid sequence of SEQ ID NO: 2 over its entire length; wherein the identity is calculated using FASTA, and parameters are set such that sequences are aligned so that the highest order match is obtained.

19. The isolated polypeptide of claim 18 which comprises the amino acid sequence of SEQ ID NO: 2.

20. The isolated polypeptide consisting of the polypeptide of SEQ ID NO: 2.

21. A polypeptide obtainable by expressing a nucleotide sequence comprising that of SEQ ID NO: 1.

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 990 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
ATGTGGGGGC TCAAGGTTCT GCTGCTACCC GTGGTGAGCT TTGCTCTATC CCCGGAGGAA    60
ACGCTGGACA CGCAGTGGGA GCTGTGGAAG AAGACCCACG GGAAGCAGTA CAACAGCAAG   120
GTGGATGAAA TCTCTCGGCG TTTAATTTGG GAAAAAAACC TGAAGAAAAT TTCTGTCCAT   180
AATCTTGAGG CCTCTCTTGG TGCCCATACG TATGAGCTGG CCATGAATCA CCTGGGAGAC   240
ATGACCAGCG AAGAAGTGGT TCAGAAGATG ACTGGACTCA GAGTGCCACC TTCGCGTTCC   300
TTCAGTAATG ACACTCTCTA TACCCCAGAG TGGGAAGGCA GAGTCCCAGA CTCCATCGAC   360
TATCGAAAGA AAGGCTATGT TACTCCAGTC AAAAACCAGG GCCAGTGTGG TTCCTGTTGG   420
GCTTTCAGCT CTGCGGGTGC CCTGGAGGGC CAACTCAAGA GAAAACTGG CAAACTCTTA   480
GCTCTGAGTC CCCAGAATCT TGTGGACTGT GTGTCTGAGA ACTATGGCTG TGGAGGCGGC   540
TATATGACCA CTGCCTTCCA ATATGTGCAG CAGAATGGAG GCATTGACTC TGAAGACGCT   600
TACCCGTATG TGGGGCAGGA TGAAAGTTGT ATGTATAACG CCACGGCAAA GGCAGCTAAG   660
TGCAGAGGGT ACAGAGAGAT CCCTGTGGGG AACGAGAAAG CCCTGAAGAG AGCAGTGGCT   720
CGGGTAGGAC CCGTCTCTGT GTCCATCGAT GCAAGCTTGA CATCTTTCCA ATTTTACAGC   780
AGAGGTGTGT ACTATGACGA AAACTGCGAC CGTGATAATG TGAACCATGC CGTGTTGGTG   840
GTGGGCTATG GCACCCAGAA GGGAAATAAG TACTGGATAA TTAAAAACAG CTGGGGAGAA   900
AGCTGGGGAA ACAAAGGCTA TGTTCTCTTG GCTCGGAATA AGAACAATGC CTGTGGCATT   960
ACCAACCTGG CCAGCTTCCC CAAGATGTGA                                    990
```

(2) INFORMATION FOR SEQ ID NO:2:

(i) SEQUENCE CHARACTERISTICS:
       (A) LENGTH: 329 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

```
Met Trp Gly Leu Lys Val Leu Leu Leu Pro Val Val Ser Phe Ala Leu
 1               5                  10                  15

Ser Pro Glu Glu Thr Leu Asp Thr Gln Trp Glu Leu Trp Lys Lys Thr
            20                  25                  30

His Gly Lys Gln Tyr Asn Ser Lys Val Asp Glu Ile Ser Arg Arg Leu
        35                  40                  45

Ile Trp Glu Lys Asn Leu Lys Lys Ile Ser Val His Asn Leu Glu Ala
    50                  55                  60

Ser Leu Gly Ala His Thr Tyr Glu Leu Ala Met Asn His Leu Gly Asp
```

-continued

```
65                  70                  75                  80

Met Thr Ser Glu Glu Val Val Gln Lys Met Thr Gly Leu Arg Val Pro
                85                  90                  95

Pro Ser Arg Ser Phe Ser Asn Asp Thr Leu Tyr Thr Pro Glu Trp Glu
               100                 105                 110

Gly Arg Val Pro Asp Ser Ile Asp Tyr Arg Lys Lys Gly Tyr Val Thr
           115                 120                 125

Pro Val Lys Asn Gln Gly Gln Cys Gly Ser Cys Trp Ala Phe Ser Ser
       130                 135                 140

Ala Gly Ala Leu Glu Gly Gln Leu Lys Lys Lys Thr Gly Lys Leu Leu
145                 150                 155                 160

Ala Leu Ser Pro Gln Asn Leu Val Asp Cys Val Ser Glu Asn Tyr Gly
               165                 170                 175

Cys Gly Gly Gly Tyr Met Thr Thr Ala Phe Gln Tyr Val Gln Gln Asn
           180                 185                 190

Gly Gly Ile Asp Ser Glu Asp Ala Tyr Pro Tyr Val Gly Gln Asp Glu
           195                 200                 205

Ser Cys Met Tyr Asn Ala Thr Ala Lys Ala Ala Lys Cys Arg Gly Tyr
    210                 215                 220

Arg Glu Ile Pro Val Gly Asn Glu Lys Ala Leu Lys Arg Ala Val Ala
225                 230                 235                 240

Arg Val Gly Pro Val Ser Val Ser Ile Asp Ala Ser Leu Thr Ser Phe
               245                 250                 255

Gln Phe Tyr Ser Arg Gly Val Tyr Tyr Asp Glu Asn Cys Asp Arg Asp
               260                 265                 270

Asn Val Asn His Ala Val Leu Val Val Gly Tyr Gly Thr Gln Lys Gly
           275                 280                 285

Asn Lys Tyr Trp Ile Ile Lys Asn Ser Trp Gly Glu Ser Trp Gly Asn
    290                 295                 300

Lys Gly Tyr Val Leu Leu Ala Arg Asn Lys Asn Asn Ala Cys Gly Ile
305                 310                 315                 320

Thr Asn Leu Ala Ser Phe Pro Lys Met
               325
```